United States Patent [19]
Fischer, Sr.

[11] Patent Number: 6,083,216
[45] Date of Patent: Jul. 4, 2000

[54] BENT CARDIAC LEAD WITH SHAPE MEMORY TORQUE COIL

[75] Inventor: Elmar R. Fischer, Sr., Lake Jackson, Tex.

[73] Assignee: Intermedics Inc., Angleton, Tex.

[21] Appl. No.: 09/225,812

[22] Filed: Jan. 5, 1999

[51] Int. Cl.$^7$ .................................................. A61M 31/00
[52] U.S. Cl. .......................... 604/530; 604/532; 606/78; 607/122; 607/123; 128/642
[58] Field of Search .................................. 604/523, 530, 604/532, 95; 607/122, 123, 88; 606/78; 128/642

[56] References Cited

U.S. PATENT DOCUMENTS

| | | | |
|---|---|---|---|
| 4,106,512 | 8/1978 | Bisping | 128/418 |
| 4,567,901 | 2/1986 | Harris | 128/786 |
| 4,913,147 | 4/1990 | Fahlstrom et al. | 128/419 P |
| 5,129,404 | 7/1992 | Spehr et al. | 128/785 |
| 5,190,546 | 3/1993 | Jervis | 606/78 |
| 5,211,183 | 5/1993 | Wilson | 128/772 |
| 5,282,845 | 2/1994 | Bush et al. | 607/128 |
| 5,415,633 | 5/1995 | Lazarus et al. | 604/95 |
| 5,492,119 | 2/1996 | Abrams | 128/642 |
| 5,531,664 | 7/1996 | Adachi et al. | 600/149 |
| 5,545,204 | 8/1996 | Cammilli et al. | 607/123 |
| 5,571,160 | 11/1996 | Nyman | 607/122 |
| 5,588,964 | 12/1996 | Imran et al. | 604/95 |
| 5,617,854 | 4/1997 | Munsif | 128/642 |
| 5,632,734 | 5/1997 | Galel et al. | 604/282 |
| 5,656,029 | 8/1997 | Imran et al. | 604/95 |
| 5,656,030 | 8/1997 | Hunjan et al. | 604/95 |
| 5,779,669 | 6/1998 | Haissaguerre et al. | 604/95 |
| 5,782,896 | 7/1998 | Chen et al. | 607/88 |
| 5,849,032 | 12/1998 | Venrooij | 607/123 |
| 5,871,444 | 2/1999 | Ouchi | 600/374 |
| 5,957,966 | 9/1999 | Schroeppel et al. | 607/122 |

OTHER PUBLICATIONS

Intermedics, Inc.; *Temporary Transcutaneous Pacing Wire Extension Lead Model 366–02*—Sales Brochure; all pages; Oct. 1982.

C. Daubert et al.; *Permanent Left Atrial Pacing with a Specifically Designed Coronary Sinus Lead*; PACE; vol. 18; p. 1180; May 1995.

Robert R. Brownlee et al.; *Toward Optimizing a Preshaped Catheter and System Parameters to Achieve Single Lead DDD Pacing*; PACE; vol. 20; pp. 1354–1358; May 1997.

CPI, Inc.; *Endotak C Physician's Manual*; all; unknown.

Spire Corporation; *SPI–Polymer™ Sales Brochure*; all; unknown.

*Primary Examiner*—John D. Yasko
*Attorney, Agent, or Firm*—Schwegman, Lundberg, Woessner & Kluth, P.A.

[57] ABSTRACT

In one aspect of the present invention, a cardiac lead is provided that includes a connector for coupling to a cardiac stimulator that has a first rotatable member, and a tubular insulating sleeve that has a first end coupled to the connector and a second end. A tip assembly is coupled to the second end. The tip assembly has a second rotatable member. A coiled wire is coupled between the first rotatable member and the second rotatable member. The coiled wire is composed of a shape-memory material and is operable to transmit torque between the first rotatable member and the second rotatable member. Where the lead is provided with a bend, the shape-memory coiled wire retains a straight set, enabling smooth rotation of a fixation corkscrew without precession of the lead tip.

39 Claims, 9 Drawing Sheets

BENT CARDIAC LEAD WITH SHAPE MEMORY TORQUE COIL

BACKGROUND OF THE INVENTION

1. Field of the Invention

This invention relates generally to cardiac stimulator leads, and more particularly to a cardiac stimulator lead having a bent insulating sleeve and a shape memory torque coil.

2. Description of the Related Art

In a typical endocardial implantation procedure, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip, or alternatively, by a passive mechanism, such as one or more radially spaced tines that engage the endocardium. The proximal end of the lead is then connected to the cardiac pacemaker or defibrillator and the incision is closed. The implantation route and site are usually imaged in real time by fluoroscopy to confirm proper manipulation and placement of the lead.

A conventional cardiac stimulator lead normally consists of an elongated flexible tubular, electrically insulating sleeve that is connected proximally to a connector that is adapted to couple to the header of a cardiac pacemaker or defibrillator, and distally to a tubular tip electrode. One or more ring-type electrodes may be secured to the sleeve at various positions along the length of the sleeve. The proximal end of the lead sleeve is connected to the connector by application of various biocompatible adhesives to various portions of the connector and the sleeve. The tip electrode ordinarily consists of a tubular structure that has an increased diameter portion that forms an annular shoulder against which the distal end of the lead sleeve is abutted. The exterior surface of the tubular structure is normally smooth as is the interior surface of the distal end of the lead sleeve.

In conventional active fixation tip electrodes, engagement with the endocardium is often achieved by twisting a corkscrew that is attached to the tip electrode into the endocardium. In many conventional designs, the corkscrew is fixed to the tip electrode and the entire lead is twisted to screw the corkscrew into the heart tissue. In another common design, the corkscrew is projectable from the tip electrode. In some of these types of designs, the corkscrew is twisted with the aid of a stylet that is inserted into the lumen of the lead. In others, a coiled wire is positioned inside the lead, and connected distally to the corkscrew and proximally to a rotatable pin. As the pin is twisted by the physician, the coiled wire transmits the applied torque from the pin to rotate the corkscrew.

Conventional torque coils commonly consist of a strand of drawn wire that has been coiled into an elongated helix. At the time the wire is drawn and coiled, the torque coil takes on a straight-set, that is, the torque coil resembles a helical spring. In cardiac leads, such torque coils are commonly constructed of biocompatible metallic materials, such as MP35N or 316L stainless steel. The straight-set torque coil is then positioned inside an initially straight length of thermally setting tubing, such as polyurethane, and connected with the various other components of the lead. The lead is then wrapped around a mandrel or some other type of jig to establish the requisite J-shape or bend and heated above a given temperature for a set time to thermally set the bent shape.

The thermal setting of the lead sleeve to establish the requisite J or bent shape normally does not effect the memory of the torque coil, as the thermal setting is carried out at a temperature that is significantly lower than the temperatures that would cause grain structure changes in the material of the torque coil. However, the bending of the lead sleeve, and thus the torque coil, does result in what is in essence a cold working of the torque coil. As a result of this cold working, the torque coil loses its straight-set memory and takes on a bent set.

With a bent-set, conventional torque coils frequently cause the tips of conventional bent leads to move unpredictably when the physician twists the torque coil during implantation. The bent portion of the torque coil will cause the tip of the lead to precess as the torque coil is twisted proximally by the physician. The movement of the tip of the lead is not unlike the precession of the axis of rotation of a spinning gyroscope, albeit in a much more erratic and unpredictable fashion. As a consequence, the physician may accurately position the tip of the lead proximate the site requiring electrical stimulation only to have the tip migrate away from the desired location after the torque coil is twisted. This difficulty can lead to a series of trial and error attempts by the physician in order to obtain the proper positioning of the lead tip. In order to compensate for the erratic and unpredictable movement of the lead tip, physicians sometimes resort to first positioning the tip near the targeted tissue and then jabbing the tip into the heart wall. The physician then relies on irregular heart tissue, such as musculi pectinati, to prevent the tip from flopping about while the torque coil is twisted. This technique may also involve some trial and error and may not work well where fixation to smooth tissue is indicated.

The present invention is directed to overcoming or reducing the effects of one or more of the foregoing disadvantages.

SUMMARY OF THE INVENTION

In accordance with one aspect of the present invention, a cardiac lead is provided that includes a connector for coupling to a cardiac stimulator that has a first rotatable member, and a tubular insulating sleeve that has a first end coupled to the connector and a second end. A tip assembly is coupled to the second end. The tip assembly has a second rotatable member. A coiled wire is coupled between the first rotatable member and the second rotatable member. The coiled wire is composed of shape-memory material and is operable to transmit torque between the first rotatable member and the second rotatable member.

In accordance with another aspect of the present invention, a cardiac lead is provided that includes a connector for coupling to a cardiac stimulator that has a first rotatable member. A tubular insulating sleeve is provided that has a semi-permanent bend, a first end coupled to the connector and a second end. A tip assembly is coupled to the second end. The tip assembly has a second rotatable member. A coiled wire is coupled between the first rotatable member and the second rotatable member. The coiled wire is composed of shape-memory material and is operable to transmit torque between the first rotatable member and the second rotatable member. An electrode is coupled to the sleeve. A conductor wire is coupled between the connector and the electrode for transmitting electric signals between the connector and the electrode.

In accordance with another aspect of the present invention, a cardiac lead is provided that includes a connector for coupling to a cardiac stimulator that has a rotatable member. A tubular insulating sleeve is provided that has a semi-permanent bend, a first end coupled to the connector and a second end. A tip electrode is coupled to the second end and has a corkscrew projectable therefrom. A coiled wire is coupled between the rotatable member and the corkscrew. The coiled wire is composed of shape-memory material and is operable to transmit torque between the first rotatable member and the corkscrew.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
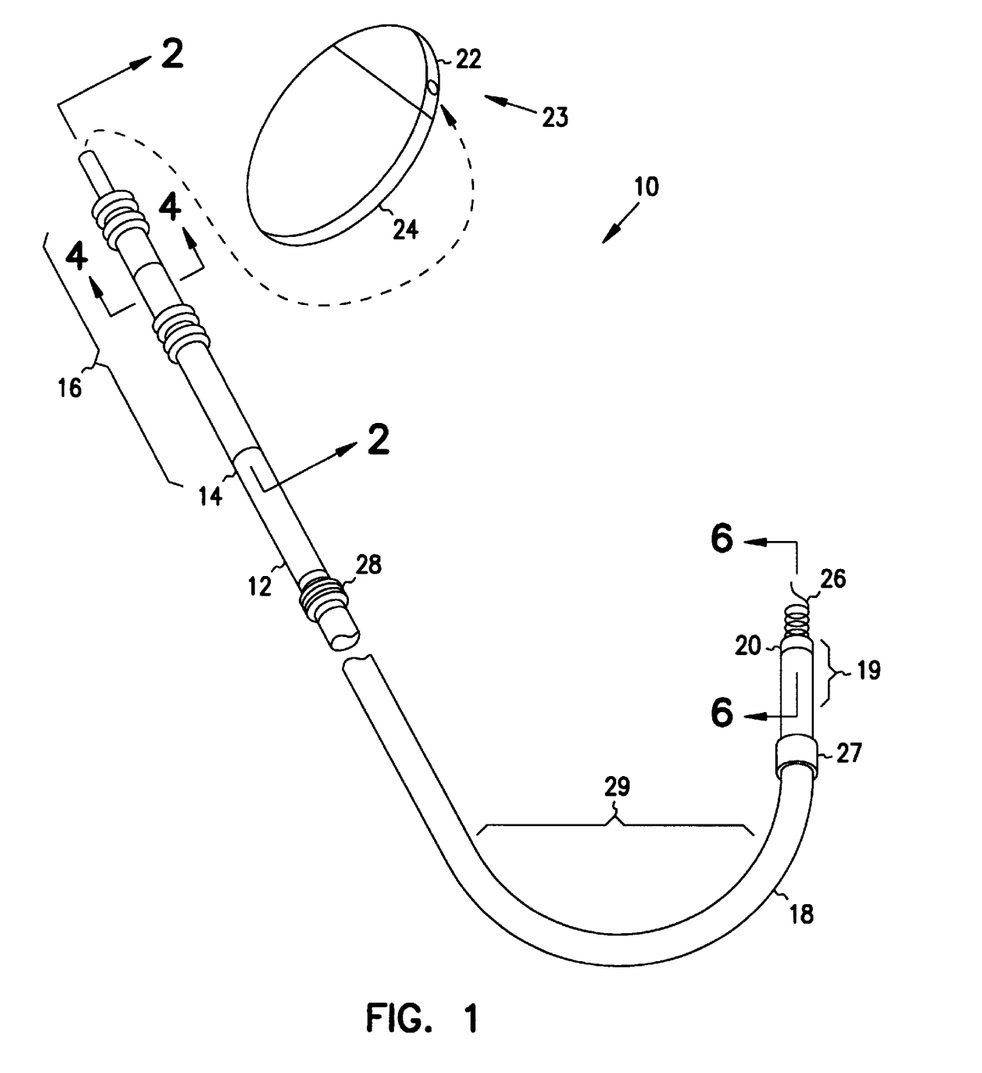
FIG. 1 is a pictorial view of an exemplary embodiment of a cardiac lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac stimulator lead 10 that includes a flexible insulating sleeve 12 that has a proximal end 14 coupled to a connector 16, and a distal end 18 coupled to a tip assembly 19 that includes a tip electrode 20. The sleeve 12 is of such length that it is shown broken. The connector 16 is designed to be inserted into the header 22 of a cardiac stimulator 23 as indicated by the dashed arrow, and is shown highly exaggerated in size relative to the cardiac stimulator 23. The header 22 is mounted to a can or housing 24. The cardiac stimulator 23 may be a pacemaker, a cardioverter/defibrillator, or other type of stimulator or a sensing instrument. The tip electrode 20 is provided with a corkscrew 26 projectable therefrom to engage and actively secure the lead 10 to myocardial tissue. The illustrated embodiment of the lead 10 is bipolar. Accordingly, the distal end 18 is provided with an electrode 27 located proximal to the tip electrode 20. However, unipolar or other multi-polar arrangements are possible as well. A suture sleeve 28 may be slipped over the sleeve 12. During implantation, the suture sleeve 28 is sewn to body tissue at the site of transvenous entry.

The sleeve 12 is a tubular member that provides a robust, electrically insulating coupling between the connector 16 and the electrode 20, as well as a protective jacket to shield one or more fine gage conductor wires enclosed therein from body fluids and tissues. The distal end 18 of the sleeve 12 is provided with a semi-permanent bend 29 to enable the corkscrew 26 to be positioned in areas of the heart that require a significant curvature of the lead 10 to reach, such as, for example, the appendix auriculae of the right auricle or near the semilunar valves of the pulmonary artery. As used herein, the phrase "semi-permanent" is intended to mean that the bend 29 is set in the sleeve 12 sometime prior to implantation with the sleeve 12 retaining sufficient elasticity so that the bend 29 may be readily straightened temporarily by hand or with the aid of a stylet at the time of transvenous entry, and allowed to recover after insertion into the heart. The recovery will normally be initiated by removal of the stylet.

As set forth in detail below, the manner in which the semi-permanent bend 29 is set will depend in part on the material(s) used for the sleeve 12. In general, the entirety or some lesser portion of the sleeve 12 is advantageously composed of a biocompatible, electrically insulating material that may be thermoset to establish the semi-permanent bend 29. In an exemplary embodiment, the sleeve 12 is composed of polyurethane or the like. As used herein, the phrase "composed of" is not intended to exclude the combining of a given material, such as polyurethane, with another material(s). If polyurethane is selected, the lead 10, including the sleeve 12, may be initially constructed with a straight or unbent shape. The distal portion of the lead 10 may then be spooled around a cylindrical fixture (not shown) and heated to above about 105° C. for a sufficient time to achieve saturation. The lead 10 may then be cooled at room temperature to set the semipermanent bend 29 and removed from the fixture.

Figure 2:
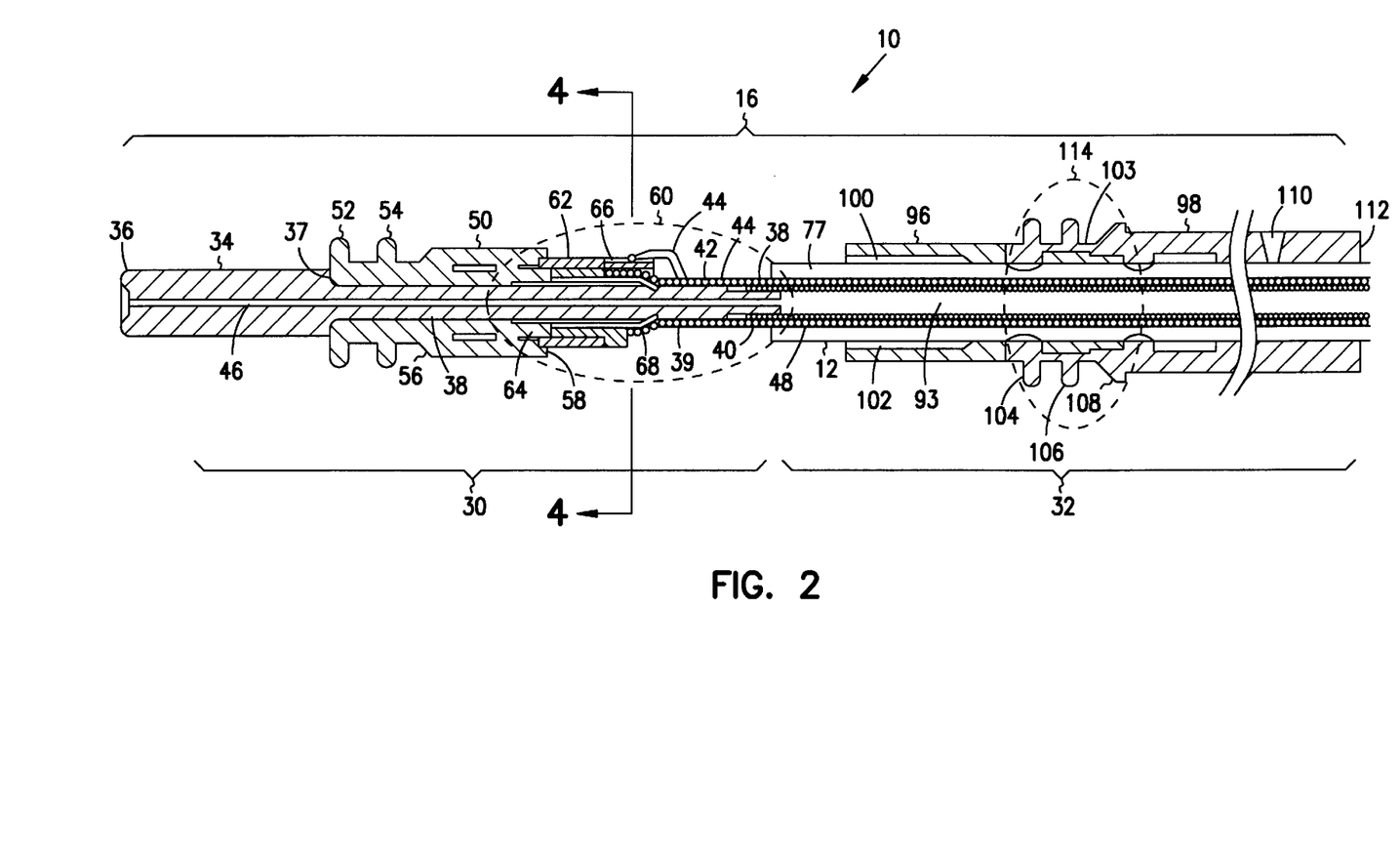
FIG. 2 is a cross-sectional view of the cardiac lead of FIG. 1 taken at section 2—2 in accordance with the present invention.

The detailed structure of the connector 16 may be understood by referring now to FIG. 2, which is a cross-sectional view of FIG. 1 taken at section 2—2. The connector 16 includes a connector pin assembly 30 coupled to a connector sleeve assembly 32. For clarity of illustration, the connector pin assembly 30 and the connector sleeve assembly 32 are shown exploded. The connector pin assembly 30 includes a rotatable or tubular pin member 34 that has an elongated proximal end 36 designed to make electrical contact with one or more electrical contacts inside the cardiac stimulator 24 depicted in FIG. 1, and serves as a handle for twisting the pin 34 to manipulate the corkscrew 26 as described below. The distal end of the pin 34 consists of an intermediate shank 38 that tapers down from the proximal end 36 to establish an annular shoulder 37, an intermediate shank 39, and a distal shank 40. The intermediate shank 39 is suitably sized to accommodate the nested coils of a conductor wire 42 and another conductor wire 44. The distal shank 40 is sized to receive the coils of a torque coil 48. The wire 42 is electrically connected distally to the tip electrode 20 depicted in FIG. 1, and the wire 44 is electrically connected distally to the annular electrode 27 depicted in FIG. 1. The connections of the wires 42 and 44 to the pin assembly 30 will be described in more detail below. A lumen 46 extends through the pin member 34.

A first insulating sleeve 50 is coupled to the exterior of the pin member 34. The first insulating sleeve 50 includes longitudinally spaced-apart O-rings 52 and 54 that are designed to engage structures within the cardiac stimulator 24 shown in FIG. 1 and to provide a seal for the pin member 34 against the intrusion of body fluids following implantation. A single O-ring may be used in place of the pair 52 and 54. The first insulating sleeve 50 is provided with a proximally facing chamfer surface 56 that is principally designed to provide a tapered surface to facilitate easy insertion of the connector 16 into the cardiac stimulator 24 shown in FIG. 1. The distal end of the first insulating sleeve 50 includes a distally facing annular surface 58 against which the conductor sleeve assembly 32 is abutted when the connector 16 is assembled. The first insulating sleeve 50 is advantageously composed of a biocompatible flexible material that may be advantageously injection molded around the pin member 34. The material may be silicone, polyurethane, or like materials. In this way, the O-rings 52 and 54 may be formed integrally with the first insulating sleeve 50. Alternatively, the first insulating sleeve 50 may be provided with external grooves and the O-rings 52 and 54 secured to the first insulating sleeve 50 as separate members.

Figure 3:
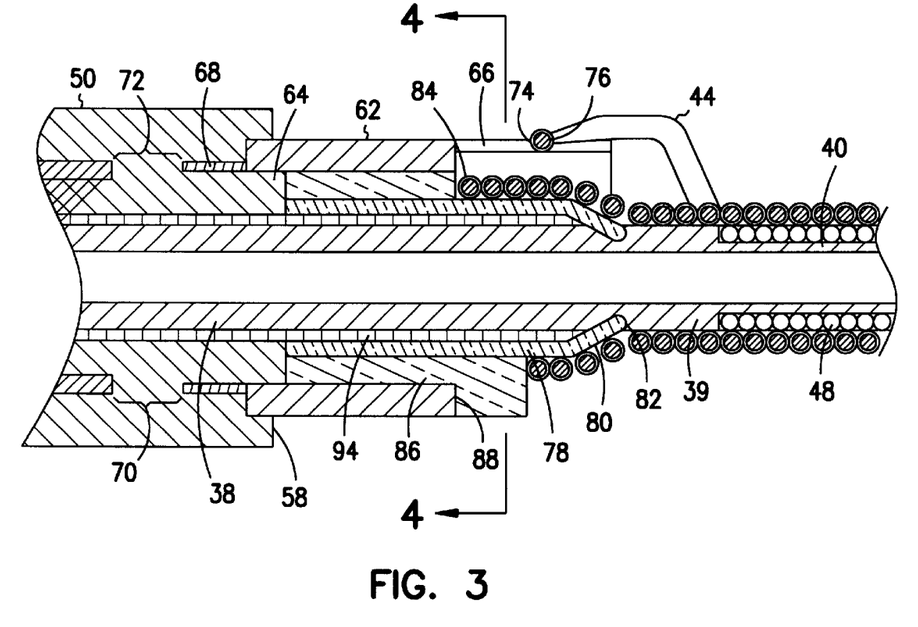
FIG. 3 is a close-in view of a portion of the lead shown in FIG. 2 depicting the rotatable pin member in accordance with the present invention.
Figure 4:
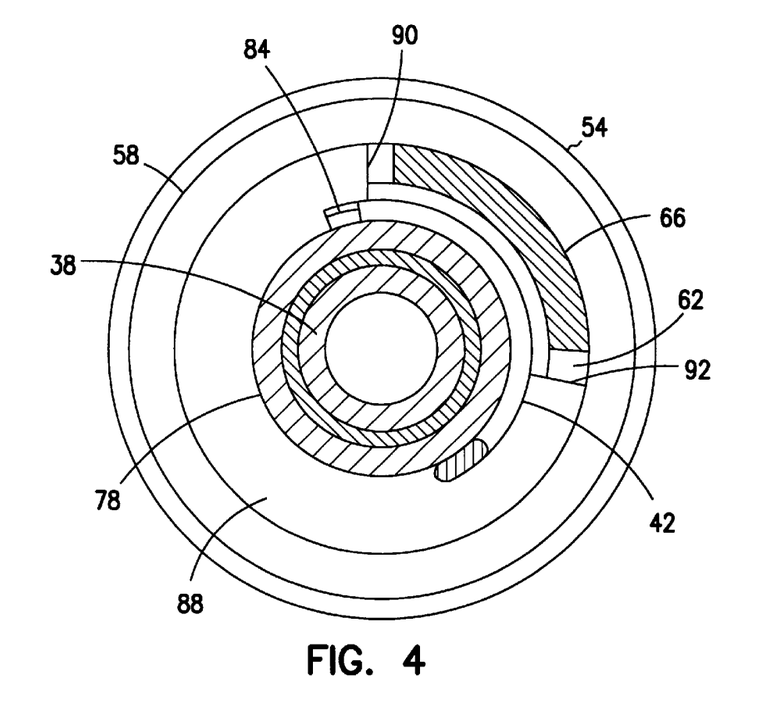
FIG. 4 is a cross-sectional view of FIGS. 2 and 3 taken at section 4—4 in accordance with the present invention.

Referring now also to FIG. 3, which is a detailed view of the portion of FIG. 2 circumscribed by the dashed oval 60, and to FIG. 4, which is a cross-sectional view of FIG. 3 taken at section 4—4, an annular member 62 is disposed around a reduced diameter portion 64 of the sleeve 50. The annular member 62 includes a distally projecting flag 66 to which the conductor wire 44 is attached and which provides an electrical pathway between the wire 44 and a contact (not shown) within the cardiac stimulator 24 shown in FIG. 1. The annular member 62 includes a proximally projecting reduced diameter nipple 68 that projects into the first insulating sleeve 50. The nipple has two or more circumferentially spaced ports 70 and 72 that enable molded structure to harden therein and provide a secure mechanical engagement between the first insulating sleeve 50 and the annular member 62. The flag 66 is provided with an external circumferential groove 74 that is dimensioned to receive the stripped end 76 of the conductor wire 44. The stripped end 76 is secured to the flag 66 by laser welding or like welding techniques.

As best seen in FIG. 2, the sleeve 12 is provided with a longitudinally extending slot 77 that is slightly wider than the outer diameter of the wire 44. The slot 77 provides a space to accommodate the wire 44 so that the sleeve 12 may be pushed past the wire 44 and abutted against the reduced diameter portion 64.

Referring again to FIGS. 3 and 4, electrical connection between the conductor wire 42 and the pin member 34 is established by a cylindrical contact sleeve 78 through which the pin member 34 is journalled and which is disposed partially within the annular member 62. The contact sleeve 78 abuts proximally against the reduced diameter portion 64 and is provided distally with an inwardly tapering portion 80 that engages a notch in the pin member 34 at 82. The engagement between the tapered portion 80 and the notch 82 serves to retain the pin member 34 within the connector pin assembly 30. As discussed more below, the pin member 34 is rotated to extend and/or retract the corkscrew 26 depicted in FIG. 1. The skilled artisan will appreciate that if the conductor wire 42 is allowed to rotate with the pin member 34, the wire 42 may become damaged or provide undesirable resistance to the rotation of the pin member 34. Accordingly, the fit provided between the tapered portion 80 and the notch 82 is such that the pin member 34 may readily be rotated relative to the fixed contact sleeve 78 while still maintaining sufficient contact between the pin member 34 and the contact sleeve 80 such that electrical conductivity between the conductor wire 42 and the pin member 34 is retained. As best seen in FIG. 4, the wire 42 is stripped at 84 and secured to the contact sleeve 78 by laser welding or like techniques. Electrical isolation between the annular member 62 and the contact sleeve 78 is provided by an annular bushing 86 that includes distally disposed annular flange 88 shoulders against the distal end of the annular member 62. The flange is not coextensive with the entire circumference of the bushing 86. Instead, the flange 78 includes a cutout, best seen in FIG. 4, extending from the surface 90 to the surface 92. The cutout is provided to accommodate the flag 66.

The embodiment depicted in FIGS. 1, 2, 3, and 4, is bipolar. However, a unipolar arrangement may be implemented by incorporating a single conductor wire, such as the wire 42, that is coupled to either the pin member 34 or to the flag 66, or by using the torque coil 48 as a conductor. The conductor wires 42 and 44 are depicted as individually insulated conductors jacketed with an insulating coating of ETFE or the like. The insulation is stripped at the ends of the wires 42 and 44 prior to welding to contact sleeve 68 and the flag 66. However, the skilled artisan will appreciate that the conductor wires 42 and 44 may not be individually insulated if the lead 10 is unipolar or if the various conductor wires in the lead 10 are coaxially arranged or arranged in a nested configuration.

Figure 6:
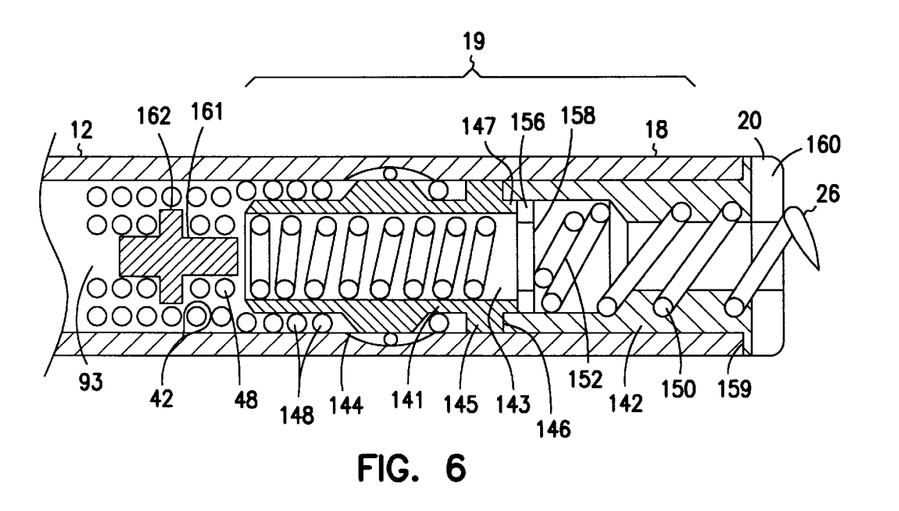
FIG. 6 is a cross-sectional view of FIG. 1 taken at section 6—6 in accordance with the present invention.

Referring again specifically to FIGS. 2 and 3 and also to FIG. 6, the torque coil 48 is a coiled wire that is secured proximally to the distal shank 40 and distally to the corkscrew 26 by laser welding, crimping or the like. The torque coil 48, as the name implies, is designed to transmit torque from the pin member 34 to the corkscrew 26 in order to deploy the corkscrew 26. The skilled artisan will appreciate that, in lieu of the corkscrew 26, another type of rotatable member may be positioned in the tip assembly 19 and rotated via the torque coil 48. The torque coil 48 may consist of a single coiled filar or multiple coiled filars. The pitch of the individual coils in the torque coil 48 is largely a matter of design discretion. However, the skilled artisan will appreciate that as the pitch of the coils is increased, the torque carrying capabilities of the coil 48 will decrease unless the stiffness of the material used to fabricate the coil 48 is proportionally increased. In the illustrated embodiment, the torque coil 48 is close-wound, resulting in very little separation between adjacent coils.

The torque coil 48 is designed to exhibit biocompatibility and sufficient stiffness to transmit the torque required to twist the corkscrew 26. In addition to these basic requirements, the torque coil 48 is intended to enable deployment of the corkscrew 26 without the unpredictable precession of the distal end 18 of the lead sleeve 12 that is often associated with conventional torque coil designs. In this regard, the torque coil 48 is advantageously fabricated from a material that is resistant to acquiring a bent set following establishment of the semi-permanent bend 29 in the lead sleeve 12 shown in FIG. 1. Nickel-titanium alloys with the formula $Ni_xTi_y$, where x and y indicate the relative ratios of nickel and titanium, represent an example of such shape-memory materials. Various $Ni_xTi_y$ alloys are commercially available from various manufacturers under the tradename NITINOL.

Assume for the purpose of illustration that the torque coil 48 is fabricated from NITINOL. The NITINOL is initially drawn into wire, and the wire is then coiled into a helix at a temperature above the phase transition temperature for the alloy and allowed to set. The finished torque coil 48 is thus provided with a straight set, and resembles a relatively straight helical spring. The shape-memory characteristics of the $Ni_xTi_y$ alloy enable the torque coil 48 to retain the straight set even after the semi-permanent bend 29 (See FIG. 1) is set in the lead sleeve 12. Thus, the coil 48 will not cause the distal end 18 of the lead sleeve 12 to wobble when twisted by the pin 34.

The inner diameter of the torque coil 48 as well as the diameter filar(s) that make up the torque coil 48 are largely matters of design discretion. In an exemplary embodiment, the inner diameter of the torque coil 48 may be about 0.005 to 0.03 inches. This range can accommodate many commonly used stylets. The diameter of the filar(s) may be about 0.002 to 0.004 inches.

Still referring to FIGS. 2 and 3, it is desirable to electrically isolate the annular member 62 from the pin member 34 to alleviate the potential for short circuiting. This is particularly important during electrical verification testing, which is normally done at relatively high voltage. The primary electrical insulation is provided by the first insulating sleeve 50, and particularly the reduced diameter portion 64, as well as the bushing 86. It is anticipated that the material used to fabricate the first insulating sleeve 50 will readily fill the space, and provide a complete electrically insulating separation between the annular member 62 and the pin member 34. However, the skilled artisan will appreciate that there is the possibility of void formation during the molding process due to air bubbles or other mechanisms. If a void is formed in the reduced diameter portion 64 between the annular member 62 and the pin member 34, destructive arcing may occur in the void during high voltage electrical verification testing of the lead 10. To reduce the possibility of shorts through a void formed in the reduced diameter portion 64, an insulating annular member 94 may be slipped over the intermediate shank 38 and abutted proximally against the shoulder 37 prior to molding of the first insulating sleeve 50. The insulating annular member 94 may be composed of a variety of biocompatible insulating materials such as, for example, polyimide, polyurethane, or like materials.

Referring to FIG. 2, the connector sleeve assembly 32 includes a conductor sleeve 96 that is coupled to a second insulating sleeve 98. The second insulating sleeve 98 is a tubular member of such length and the scale of FIG. 2 is such that the second insulating sleeve 98 is shown broken. The conductor sleeve 96 includes a proximally disposed bore 100 that is dimensioned so that the conductor sleeve 96 may be readily slipped over the annular member 62 until the annular surface 102 of the conductor sleeve 96 abuts the annular shoulder 58 of the first insulating sleeve 50. The conductor sleeve 96 is designed to establish an electrical pathway between the annular member 62 and a conducting structure inside the cardiac stimulator 24 shown in FIG. 1. Accordingly, the fit between the internal diameter of the conductor sleeve 96 and the outer diameter of the annular member 62 should be close enough to provide good electrical contact. The conductor sleeve 96 is coupled to the annular member 62 by laser welding or like techniques.

The proximal end 103 of the second insulating sleeve 98 is provided with two longitudinally spaced-apart O-rings 104 and 106 that serve to seal the conductor sleeve 96 against the intrusion of body fluids after the lead 10 is coupled to the cardiac stimulator 24 shown in FIG. 1. As with the aforementioned O-rings 52 and 54, the O-rings 104 and 106 may be integrally molded into the second insulating sleeve 98 or attached as separate members. On the distal side of the O-ring 106, the second insulating sleeve 98 expands in diameter and defines a chamfer surface 108 that provides the same functionality as the chamfer surface 56, albeit in conjunction with a different portion of the internal structure of the cardiac stimulator 24 shown in FIG. 1. The internal diameter of the second insulating sleeve 98 is generally dimensioned to provide a sliding fit with the outer surface of the sleeve 12 to permit easy assembly. The second insulating sleeve 98 is secured to the sleeve 12 by a suitable biocompatible medical grade adhesive, such as silicone, or any of a variety of two stage adhesives. To facilitate the introduction and spreading of the adhesive, the second insulating sleeve 98 is provided with a port 110. Adhesive is introduced into the port 110 under slight pressure to encourage the rapid and uniform spreading of the adhesive around the sleeve 12. The flow characteristics of the adhesive may be enhanced by thinning with a suitable diluent, such as heptane, prior to injection through the port 110. In addition, adhesive is back filled between the second insulating sleeve 98 and the sleeve 12 by injection under slight pressure at the interface designated 112.

Figure 5:
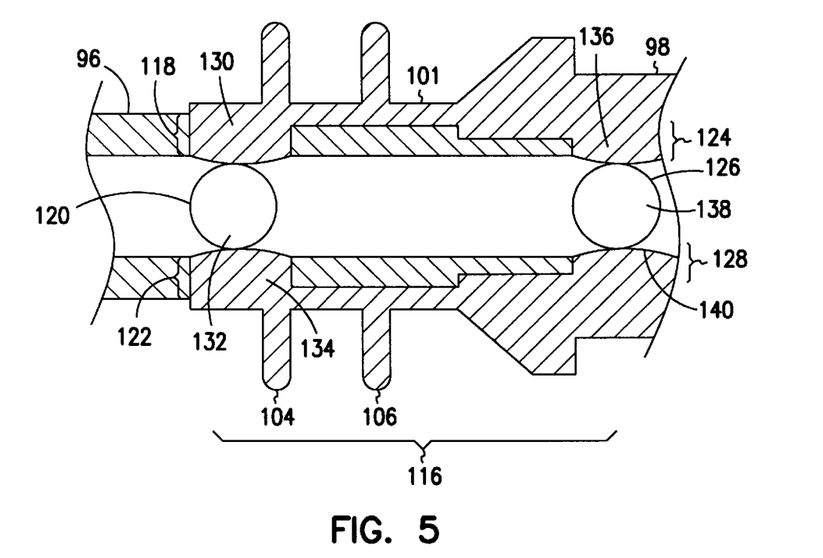
FIG. 5 is a close-in view of a portion of the lead shown in FIG. 2 depicting another portion of the connector in accordance with the present invention.

The connection between the conductor sleeve 96 and the second insulating sleeve 98 may be more readily understood by referring now to FIG. 5, which is a magnified view of the portion of FIG. 2 circumscribed by the dashed oval 114. Note that in FIG. 5, the sleeve 12 is not shown for clarity of illustration. A central portion 116 of the conductor sleeve 96 is provided with a plurality of circumferentially spaced bores, six of which are depicted at 118, 120, 122, 124, 126, and 128. The bores 118, 120, 122, 124, 126, and 128 are designed to enable the material used to mold the second insulating sleeve 98 to flow into the bores 118, 129, 122, 124, 126, and 128 and harden into buttons 130, 132, 134, 136, 138, and 140. The engagement between the buttons 130, 132, 134, 136, 138, and 140 and the central portion 116 of the conductor sleeve 96 establishes a secure mechanical engagement between the conductor sleeve 96 and the second insulating sleeve 98. The second insulating sleeve 98 is advantageously composed of the same types of materials used to fabricate the first insulating sleeve 50 shown in FIG. 2, and is advantageously injection molded.

The pin member 34, the annular member 62, and the conductor sleeve 96 are advantageously composed of a biocompatible conducting material that may be welded via laser or like techniques. Exemplary materials include 316L stainless steel, other suitable types of stainless steel, MP35N, or like materials.

The connector 16 depicted in FIGS. 1, 2, 3, 4, and 5, eliminates the necessity for the conventionally used tubular crimping members and the attendant difficulties in establishing consistent and reliable crimped connections between the conductor wires of the lead and the various crimping members. Reliable electrical and mechanical connection between the conductor wires 42 and 44 and the connector 16 are established by welding. The use of welded connections in lieu of crimping tubes or slugs permits interim inspection and testing of the wire-to-connector connections and more rapid assembly.

The detailed structure of the tip assembly 19 may be understood by referring now to FIG. 6, which is a cross-sectional view of FIG. 1 taken at section 6—6. The tip assembly 19 includes the tip electrode 20, which consists of a tubular shank 141 coupled to another tubular shank 142 and sharing a common, centrally disposed bore 143. The shank 141 includes a proximally disposed flange 144 and a distally positioned flange 145. The flange 145 abuts the proximal end 146 of the shank 142, and terminates short of the distal end of the shank 141 so that a distally facing annular shoulder 147 projects into the shank 142. Alternatively, the structure of the shanks 141 and 142 may be incorporated into a single piece.

The distal coils 148 of the conductor wire 42 are spiraled around the shank 141 so that at lease one coil 148 is disposed between the flange 144 and the flange 145. This provides a mechanical capture of the coil or coils 148 to secure the wire 42 to the shank 141. The wire 42 is stripped distally to establish a conductive path to the shank 141. The wire 42 may also be secured by laser welding, other like welding techniques, or other suitable fastening methods. The main body of the shank 141 is provided with an outer diameter that is slightly larger than the inner diameter of the coils 148 of the wire 42, but smaller than that of the flanges 144 and 145. The distal coils 148 may be connected to the shank 141 by first urging the coils 148 over the main body of the shank 144 and then over the flange 144, and finally by welding, if desired.

The shank 142 is provided with a set of internal grooves or threads 150 dimensioned to receive the corkscrew 26, which is shown in a partially extended position in FIG. 6. The corkscrew 26 is connected proximally to the torque coil 48 at 152 by laser welding crimping or the like. Rotation of the torque coil 48 causes the corkscrew 26 to rotate. As the corkscrew 26 rotates, the threads 150 urge the corkscrew 26 to extend from or retract into the bore 143, depending on the direction of rotation and the type of threads, i.e., left or right handed. The number of threads 150 is a matter of discretion.

An annular washer 156 having a central aperture 158 is disposed inside the shank 142 and abutted against the annular shoulder 147 of the shank 141. The washer 156 is designed to provide some restriction to the influx of body fluids into the lumen 93 of the sleeve 12. The washer 156 may be composed of a variety of biocompatible flexible materials, such as, silicone, polyurethane, or like materials. The aperture 158 is provided and sized to accommodate the torque coil 48.

The shanks 141 and 142 are inserted into the distal end 18 of the sleeve 12. The tip of the shank 142 is provided with an expanded diameter to establish a proximally facing annular shoulder 159 against which the distal end 18 is abutted. To secure the electrode 20 to the sleeve 12, a biocompatible adhesive is applied to the exterior of the shanks 141 and 142 prior to insertion into the distal end 18 of the sleeve 12. The adhesive may be a suitable medical grade adhesive, such as silicone based adhesive, a two-part adhesive, or similar adhesives. The electrical transmission capability of the tip is enhanced by increasing the surface thereof exposed to myocardial tissue. In this regard, one or more slots 160 are provided in the face of the tip.

The shank 142 may be fabricated from a variety of biocompatible conducting materials, such as iridium oxide coated titanium, MP35N, stainless steel, platinum-iridium alloy consisting of approximately 90% platinum and 10% iridium, or some other biocompatible conducting metal, or a semiconductor material, such as silicon, or other semiconductor material.

It is desirable for the implanting physician to be able to readily verify deployment of the corkscrew 26 during implantation. In conventional lead designs, this task is often difficult due to the lack of radiopacity of conventional corkscrews. To alleviate this difficulty, a portion of the electrode 20 is composed of a suitable biocompatible radiopaque material, such as, platinum iridium alloy (90% platinum, 10% iridium, or other suitable radiopaque material. In this example, the shank 141 is composed of radiopaque material. The shank 141 thus provides a radiopaque marker of fixed position, that is, fixed relative to the sleeve 12 and the electrode 20, and as such, serves as a position benchmark. In addition, a radiopaque member or slug 161 is coupled to the torque coil 48, and thus to the corkscrew, by nesting the slug 161 inside the coil 48 as shown, or by making the slug 161 tubular and nesting it around the torque coil 48. In the embodiment illustrated in FIG. 6, the slug 161 consists of a cylindrical member having a radially outwardly projecting flange 162 that is disposed between adjacent coils of the torque coil 48 and provides a means of preventing the slug 161 from moving axially independently of the coils 48. If desired, the slug 161 may also be welded to the torque coil 48.

Prior to manipulation of the torque coil 48 to extend or retract the corkscrew 26, the initial axial separation of the slug 161 and the shank 141 may be readily determined via fluoroscopy. During extension or retraction, the torque coil 48 is rotated resulting in an axial movement of the corkscrew 26, and both the torque coil 48 and the slug 161 while the shank 141 remains fixed. The change in axial spacing between the slug 161 and the shank 141 may be easily observed under fluoroscopy. Thus, a ready method of quickly verifying the extension and/or the retraction of the corkscrew 26 is provided.

The extension and retraction operations of the lead 10 may be understood by referring now to FIGS. 1, 2, and 6. The lead 10 is implanted endocardially and the electrode 20 is positioned proximate the targeted myocardial tissue, typically by using a stylet (not shown) that is inserted through the pin member 34 and advanced down the lumen 93 of the sleeve 12. Through a combination of axial force applied on the proximal end of the lead 10 and manipulation of the stylet, the tip electrode 20 is brought into physical engagement with myocardial tissue. To extend the corkscrew 26 and engage the myocardial tissue, the pin member 34 is twisted by hand either clockwise or counterclockwise, depending upon whether the grooves in the shank 144 are right-handed or left-handed. Torque transmitted to the pin member 34 by hand is, in turn, transmitted to the corkscrew 26 via the torque coil 48. Extension of the corkscrew 26 out of the shank 144 may be verified through fluoroscopy or other imaging techniques by observing the movement of the radiopaque slug 161 in relation to the shank 141. After the corkscrew 26 has been fully extended, successful engagement with myocardial tissue may be verified by applying a gentle axial force to the connector by hand. An unsuccessful fixation with myocardial tissue may be determined via imaging as well as a sudden axial movement of the lead 10 in response to the applied axial force. To retract the corkscrew 26, the pin member 34 is twisted in the opposite direction.

Figure 7:
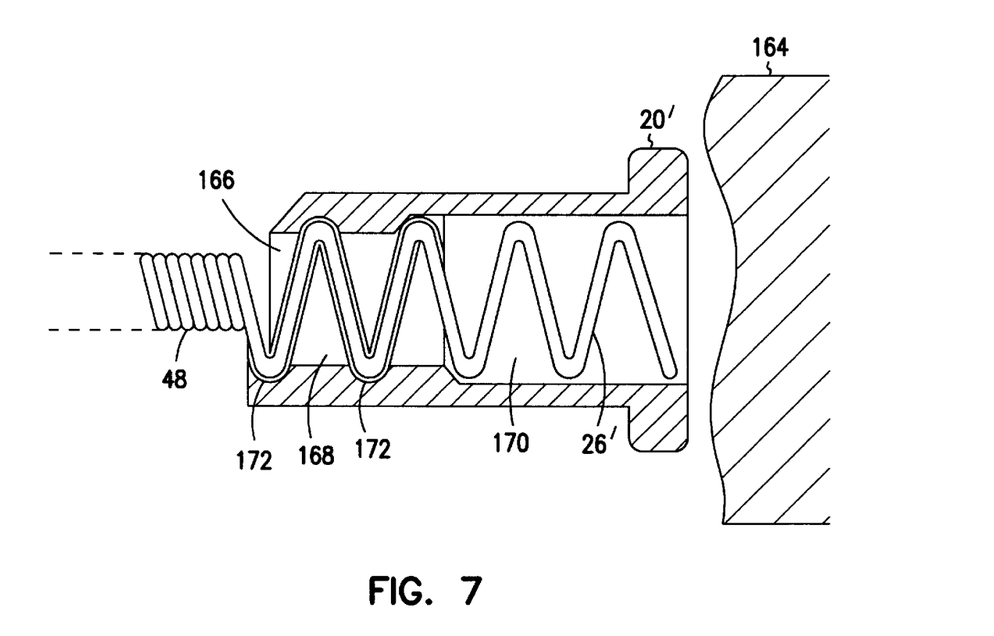
FIG. 7 is a cross-sectional view like FIG. 6 of an alternate tip electrode embodying a "smart" corkscrew in accordance with the present invention.
Figure 8:
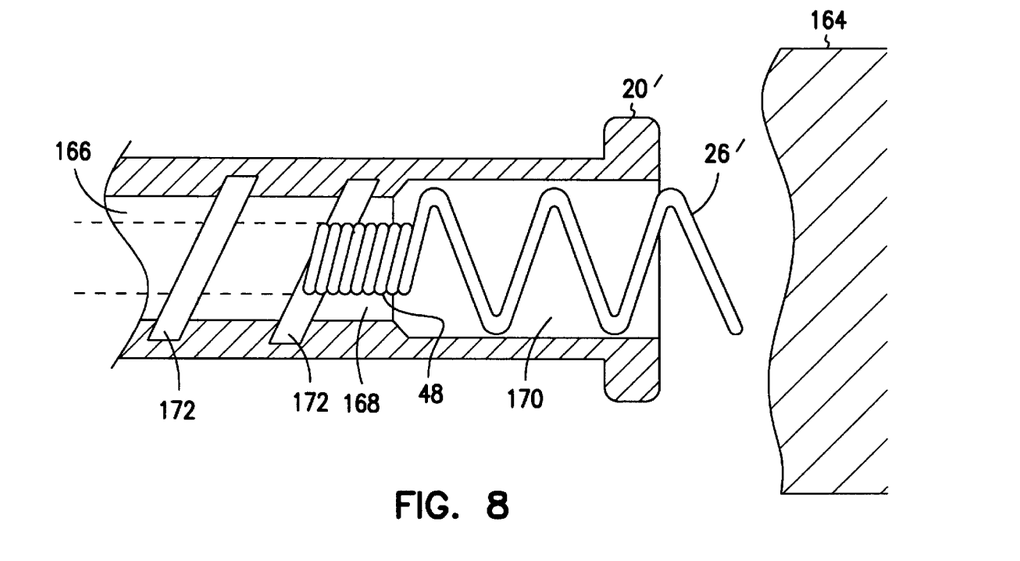
FIG. 8 is a cross-sectional view of a tip electrode depicting a "smart" corkscrew in accordance with the present invention.
Figure 9:
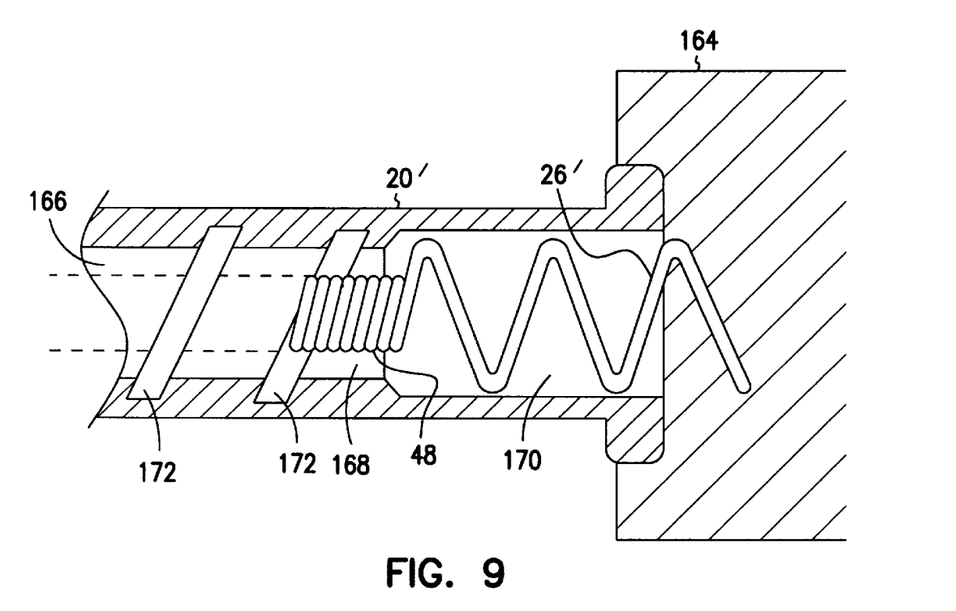
FIG. 9 is a cross-sectional view like FIG. 7 depicting partial extension of the "smart" corkscrew in accordance with the present invention.

In an alternate embodiment depicted in FIGS. 7, 8, and 9, the tip electrode, now designated 20', is provided with a "smart" corkscrew, now designated 26'. The term "smart" refers to the ability of the corkscrew 26' to fully deploy only in circumstances where the corkscrew 26' is firmly engaging and penetrating myocardial tissue 164. FIG. 7 depicts the electrode 20' with the corkscrew 26' in a fully retracted position. The electrode 20' is a tubular member provided with a longitudinally disposed lumen 166 that is divided into two sections, a first longitudinal or threaded section 168, and a second longitudinal or smooth section 170. In the threaded section 168, the electrode 20' is provided with a set of internal threads or grooves 172 that are configured similarly or identically to the grooves 150 depicted in FIG. 6. The corkscrew 26' has a first range of axial movement while engaged by the threads 172. The number of threads 172 is a matter of design discretion, though at least one is necessary to move the corkscrew 26' axially.

The smooth, i.e., unthreaded, section 170 is provided with an internal diameter that is larger than the outer diameter of the corkscrew 26' and has a relatively smooth bore to enable the corkscrew 26' to pass therethrough with little or no interference. The corkscrew 26' has a second range of axial movement where the threads 172 are not engaged.

The torque coil 48 is coupled proximally to the corkscrew 26' as described above. If a portion of the corkscrew 26' is in physical engagement with the grooves 172, as is the case in FIG. 7, torque applied to the corkscrew 26' via the torque coil 48 will produce an axial movement of the corkscrew 26' as generally described above.

The operation of this embodiment may be understood by referring now to FIGS. 8 and 9. The electrode 20' is implanted and positioned proximate myocardial tissue 164 generally as described above. Through manipulation of the torque coil 48, the corkscrew 26' is moved axially through the first range of axial movement from the fully retracted position depicted in FIG. 7 to the partially extended position shown in FIG. 8. In the partially extended position shown in FIG. 8, the corkscrew 26' has moved axially so that no portion of the corkscrew 26' is in physical engagement with the grooves 172. At this stage, the corkscrew 26' is in the second range of axial movement, and continued twisting of the torque coil 48 will simply rotate the corkscrew 26' and will not appreciably advance the corkscrew 26' axially. However, as shown in FIG. 9, when the electrode 20' is brought into physical contact with the myocardial tissue 164, further twisting of the torque coil 48 will result in the corkscrew 26' engaging and penetrating the myocardial tissue 164 axially. In this way, the corkscrew 26' will only project significantly from the electrode 20' when the corkscrew 26' is in physical engagement with myocardial tissue 164. The electrode 20' eliminates the time consuming task of retracting the corkscrew 26' into the electrode 20' by twisting the torque coil 48 in circumstances where the corkscrew 26' did not successfully engage the myocardial tissue 164 and where another attempt to attach the electrode 20' to the myocardial tissue is contemplated.

Figure 10:
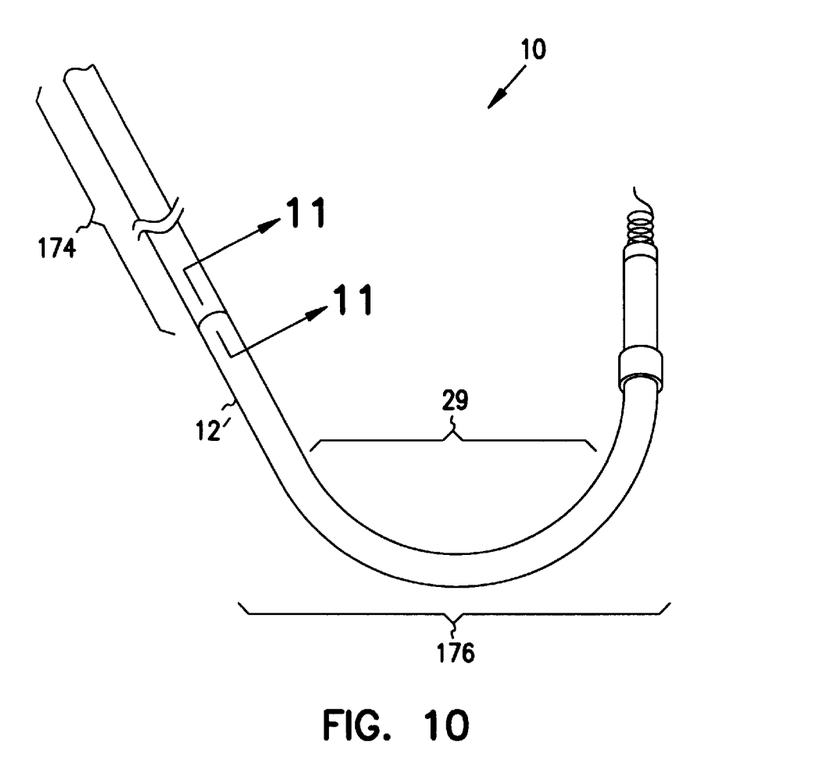
FIG. 10 is a pictorial view like FIG. 1 of an alternate exemplary embodiment of the cardiac lead in accordance with the present invention.
Figure 11:
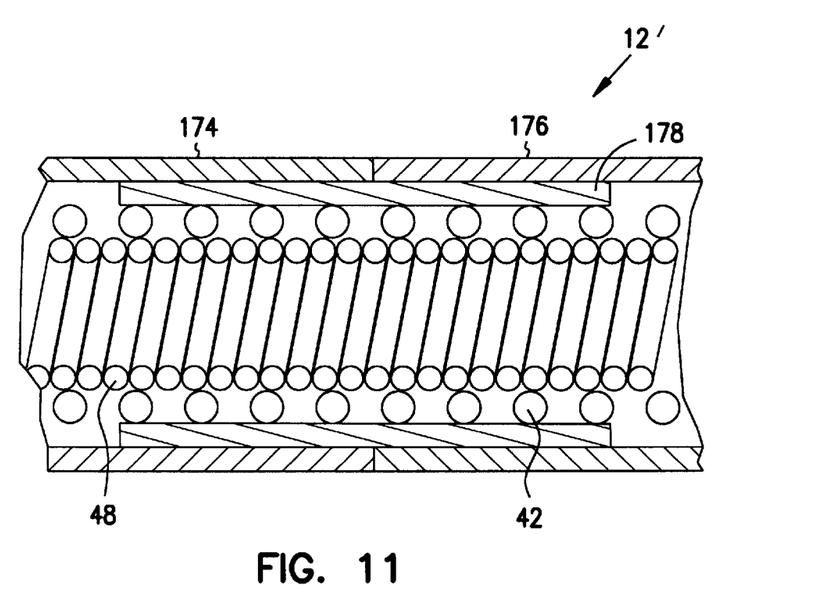
FIG. 11 is a cross-sectional view of FIG. 10 taken at section 11—11 in accordance with the present invention.

The foregoing exemplary embodiments incorporated a unitary lead sleeve composed of a thermally setting polymeric material, such as polyurethane. Alternatively, and as illustrated by the alternate exemplary embodiments depicted in FIGS. 10 and 11, 12, and 13 and 14, the lead sleeve may incorporate a portion that is capable of thermosetting and a portion that is not. The first of these alternate exemplary embodiments may be understood by referring now specifically to FIGS. 10 and 11. FIG. 11 is a cross-sectional view of FIG. 10 taken at section 11—11. For simplicity of illustration, the proximal portion of the lead 10 is not shown. In this alternate embodiment, the lead sleeve, now designated 12', consists of two segments 174 and 176 joined together by a tubular insert 178. The segment 176 is advantageously composed of a biocompatible thermally setting polymeric material, such as polyurethane or the like. The segment 174 may be composed of the same material or from a nonthermally setting biocompatible polymeric material, such as silicone or the like. The segments 174 and 176 are positioned around the tubular insert 178, abutted together and secured by a medical grade adhesive. The tubular insert 178 may be composed of a variety of biocompatible materials, such as silicone, polyurethane or the like. Biocompatible metallic materials, such as MP35N, titanium or the like may also be used where no shorting is anticipated between the tubular insert 178 and the conductor wire 42 or the torque coil 48. In this way, only the segment 176 where the semipermanent bend 29 will be introduced need be composed of a thermally setting polymeric material.

Figure 12:
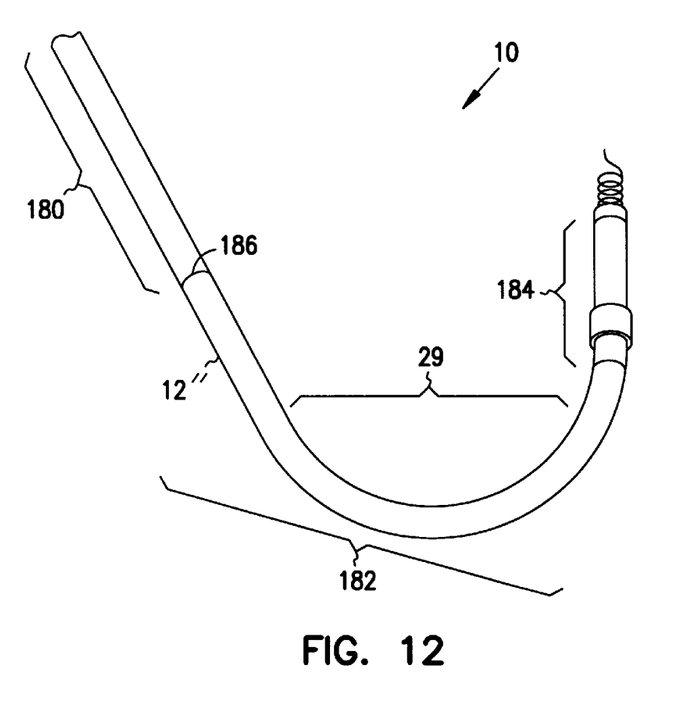
FIG. 12 is a pictorial view like FIG. 1 of another alternate exemplary embodiment of the cardiac lead in accordance with the present invention.

Another of the alternate exemplary embodiments may be understood by referring now to FIG. 12. In this alternate embodiment the lead sleeve, now designated 12", consists of three segments, 180, 182 and 184 connected in series as shown. Two adjacent segments, such as the segments 180 and 182 may be joined at the joint 186 using the structure depicted in FIG. 11. In this illustrative embodiment, the segments 180 and 184 may be composed of a nonthermally setting biocompatible polymeric material of the types described above. Similarly, the segment 182, which will be provided with the semi-permanent bend 29, may be composed of the aforementioned thermally setting materials.

Figure 13:
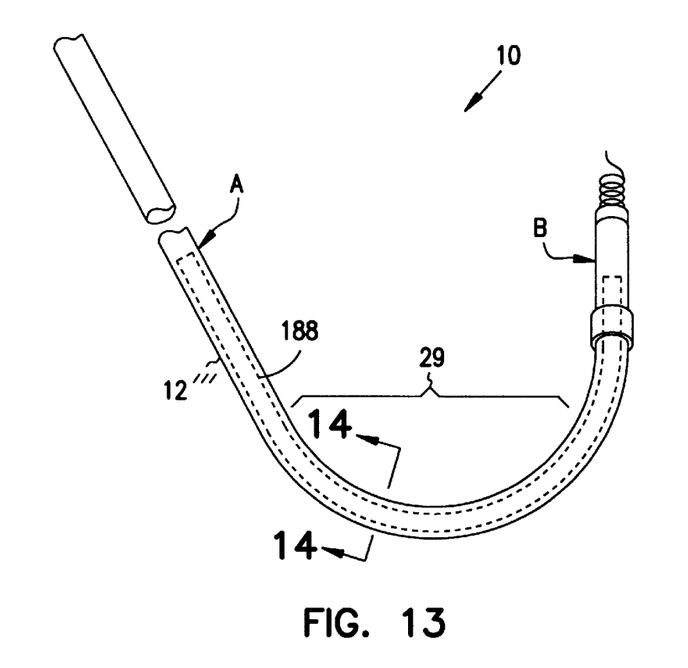
FIG. 13 is a pictorial view like FIG. 1 of another alternate exemplary embodiment of the cardiac lead in accordance with the present invention.
Figure 14:
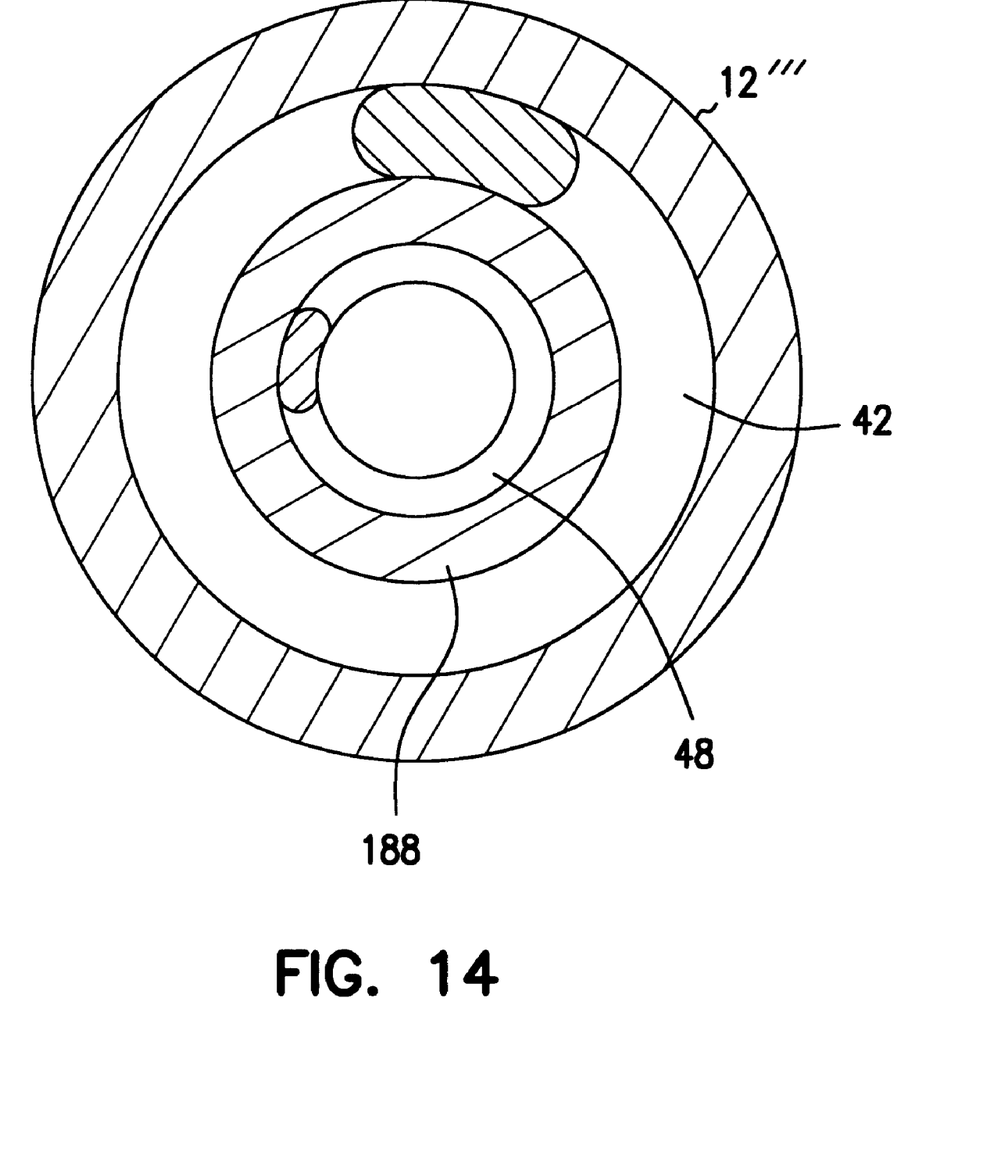
FIG. 14 is a cross-sectional view of FIG. 13 taken at section 14—14 in accordance with the present invention.

A third alternate exemplary embodiment may be understood by referring now to FIGS. 13 and 14. FIG. 14 is a cross sectional view of FIG. 13 taken at section 14—14. In this illustrated embodiment, the lead sleeve, now designated 12''', is composed of a nonthermally setting biocompatible polymeric material of the type described above. The establishment of the semipermanent bend 29 in the lead sleeve 12''' is accomplished by positioning a tubular segment 188 (shown in phantom in FIG. 13) inside the lead sleeve 12'''. The tubular segment 188 is positioned between the torque coil 48 and the conductor wire 42 as shown in FIG. 14. The tubular segment 188 is composed of a thermally setting polymeric material of the types described above. In the illustrated embodiment, the tubular segment 188 extends from point A to point B as shown in FIG. 13. However, the skilled artisan will appreciate that the length of the tubular segment 188 is largely a matter of design discretion. A relatively longer tubular insert 188 provides for greater flexibility in determining the particular shape of the semi-permanent bend 29. The embodiments depicted in FIGS. 10–14 provide for a bent lead that provides for relative rigidity in the vicinity of the bend 29 while simultaneously retaining significant flexibility in other portions of the lead 10. This composite flexibility and rigidity enables the lead 10 to be positioned in difficult to reach areas of the heart while retaining significant flexibility, particularly in the proximal portions of the lead 10 to enable those portions to readily conform to the sometimes quite irregular structures of the heart and the transvenous implantation pathway.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead, comprising:
   a connector for coupling to a cardiac stimulator and having a first rotatable member;
   a tubular insulating sleeve having a first end coupled to the connector and a second end;

a tip assembly coupled to the second end, the tip assembly having a second rotatable member; and a coiled wire coupled between the first rotatable member and the second rotatable member, the coiled wire being composed of shape-memory material and being operable to transmit torque between the first rotatable member and the second rotatable member.

2. The cardiac lead of claim 1, wherein the shape-memory material comprises a nickel-titanium alloy.

3. The cardiac lead of claim 1, wherein the first rotatable member comprises a pin for transmitting signals to and from a cardiac stimulator.

4. The cardiac lead of claim 1, wherein the second rotatable member comprises a corkscrew for engaging body tissue.

5. The cardiac lead of claim 4, wherein the tip assembly comprises a tip electrode, the corkscrew being projectable from the tip electrode.

6. The cardiac lead of claim 1, wherein the sleeve has a semi-permanent bend therein.

7. The cardiac lead of claim 1, wherein the sleeve is composed of a thermally setting polymeric material.

8. The cardiac lead of claim 1, wherein the thermally setting polymeric material comprises polyurethane.

9. The cardiac lead of claim 1, wherein the sleeve comprises a first segment composed of a a thermally setting polymeric material and a second segment coupled to the first segment and being composed of a non-thermally setting insulating material, the first segment having the semi-permanent bend.

10. The cardiac lead of claim 1, wherein the sleeve comprises a first segment composed of a a thermally setting polymeric material coupled between a second segment and a third segment composed of a non-thermally setting insulating material, the first segment having the semi-permanent bend.

11. The cardiac lead of claim 1, wherein the sleeve has a tubular segment positioned therein composed of a thermally setting polymeric material, the tubular segment having the semi-permanent bend.

12. The cardiac lead of claim 1, comprising an electrode coupled to the sleeve and a conductor wire coupled between the electrode and the connector.

13. The cardiac lead of claim 12, wherein the conductor wire comprises a conductor jacketed by an insulating coating.

14. The cardiac lead of claim 1, wherein the coiled wire comprises a single filar.

15. The cardiac lead of claim 1, wherein the coiled wire comprises a plurality of filars.

16. A cardiac lead, comprising:

a connector for coupling to a cardiac stimulator and having a first rotatable member;

a tubular insulating sleeve having a semi-permanent bend, a first end coupled to the connector and a second end;

a tip assembly coupled to the second end, the tip assembly having a second rotatable member;

a coiled wire coupled between the first rotatable member and the second rotatable member, the coiled wire being composed of shape-memory material and being operable to transmit torque between the first rotatable member and the second rotatable member;

an electrode coupled to the sleeve; and a conductor wire coupled between the connector and the electrode for transmitting electric signals between the connector and the electrode.

17. The cardiac lead of claim 16, wherein the shape-memory material comprises a nickel-titanium alloy.

18. The cardiac lead of claim 16, wherein the first rotatable member comprises a pin for transmitting signals to and from a cardiac stimulator.

19. The cardiac lead of claim 16, wherein the second rotatable member comprises a corkscrew for engaging body tissue.

20. The cardiac lead of claim 19, wherein the tip assembly comprises a tip electrode, the corkscrew being projectable from the tip electrode.

21. The cardiac lead of claim 16, wherein the sleeve is composed of a thermally setting polymeric material.

22. The cardiac lead of claim 21, wherein the thermally setting polymeric material comprises polyurethane.

23. The cardiac lead of claim 16, wherein the sleeve comprises a first segment composed of a a thermally setting polymeric material and a second segment coupled to the first segment and being composed of a non-thermally setting insulating material, the first segment having the semi-permanent bend.

24. The cardiac lead of claim 16, wherein the sleeve comprises a first segment composed of a a thermally setting polymeric material coupled between a second segment and a third segment composed of a non-thermally setting insulating material, the first segment having the semi-permanent bend.

25. The cardiac lead of claim 16, wherein the sleeve has a tubular segment positioned therein composed of a thermally setting polymeric material, the tubular segment having the semi-permanent bend.

26. The cardiac lead of claim 16, wherein the conductor wire comprises a conductor jacketed by an insulating coating.

27. The cardiac lead of claim 16, wherein the coiled wire comprises a single filar.

28. The cardiac lead of claim 16, wherein the coiled wire comprises a plurality of filars.

29. A cardiac lead, comprising:

a connector for coupling to a cardiac stimulator and having a rotatable member;

a tubular insulating sleeve having a semi-permanent bend, a first end coupled to the connector and a second end;

a tip electrode coupled to the second end and having a corkscrew projectable therefrom; and a coiled wire coupled between the rotatable member and the corkscrew, the coiled wire being composed of nickel-titanium alloy and being operable to transmit torque between the first rotatable member and the corkscrew.

30. The cardiac lead of claim 29, wherein the first rotatable member comprises a pin for transmitting signals to and from a cardiac stimulator.

31. The cardiac lead of claim 29, wherein the sleeve is composed of a thermally setting polymeric material.

32. The cardiac lead of claim 31, wherein the thermally setting polymeric material comprises polyurethane.

33. The cardiac lead of claim 29, wherein the sleeve comprises a first segment composed of a a thermally setting polymeric material and a second segment coupled to the first segment and being composed of a non-thermally setting insulating material, the first segment having the semi-permanent bend.

34. The cardiac lead of claim 29, wherein the sleeve comprises a first segment composed of a a thermally setting polymeric material coupled between a second segment and a third segment composed of a non-thermally setting insulating material, the first segment having the semi-permanent bend.

35. The cardiac lead of claim 29, wherein the sleeve has a tubular segment positioned therein composed of a thermally setting polymeric material, the tubular segment having the semi-permanent bend.

36. The cardiac lead of claim 29, comprising an electrode coupled to the sleeve and a conductor wire coupled between the electrode and the connector.

37. The cardiac lead of claim 36, wherein the conductor wire comprises a conductor jacketed by an insulating coating.

38. The cardiac lead of claim 29, wherein the coiled wire comprises a single filar.

39. The cardiac lead of claim 29, wherein the coiled wire comprises a plurality of filars.

* * * * *

UNITED STATES PATENT AND TRADEMARK OFFICE
CERTIFICATE OF CORRECTION

PATENT NO.: 6,083,216
DATED: Jul. 4, 2000
INVENTOR(S): Fischer, Sr.

It is certified that errors appear in the above-identified patent and that said Patent is hereby corrected as shown below:

In column 13, line 28, delete "a"; second occurrence.

In column 13, line 35, delete "a"; second occurrence.

In column 14, line 25, delete "a"; second occurrence.

In column 14, line 31, delete "a"; second occurrence.

In column 15, line 6, delete "a"; second occurrence.

In column 15, line 12, delete "a"; second occurrence.

Signed and Sealed this

Tenth Day of April, 2001

*Attest:*

NICHOLAS P. GODICI

*Attesting Officer*  *Acting Director of the United States Patent and Trademark Office*